US00PP33340P2

(12) United States Plant Patent
van der Arend

(10) Patent No.: US PP33,340 P2
(45) Date of Patent: Aug. 10, 2021

(54) ***PHILODENDRON* PLANT NAMED 'PPIPVE007'**

(50) Latin Name: *Philodendron verrucosum*
Varietal Denomination: PPIPVE007

(71) Applicant: Rene P. A. van der Arend, Naaldwijk (NL)

(72) Inventor: Rene P. A. van der Arend, Naaldwijk (NL)

(73) Assignee: Plant Planet International B.V., Naaldwijk (NL)

( * ) Notice: Subject to any disclaimer, the term of this patent is extended or adjusted under 35 U.S.C. 154(b) by 0 days.

(21) Appl. No.: 16/945,761

(22) Filed: Jul. 31, 2020

(51) Int. Cl.
*A01H 5/12* (2018.01)
*A01H 6/10* (2018.01)
*A01H 5/02* (2018.01)

(52) U.S. Cl.
USPC ..... Plt./381
CPC ..... *A01H 6/10* (2018.05); *A01H 5/02* (2013.01)

(58) Field of Classification Search
USPC ..... Plt./381
See application file for complete search history.

*Primary Examiner* — Annette H Para
(74) *Attorney, Agent, or Firm* — C. Anne Whealy

(57) ABSTRACT

A new and distinct cultivar of *Philodendron* plant named 'PPIPVE007', characterized by its relatively compact, upright and uniform plant habit; moderately vigorous growth habit; and relatively large leaves that are dark green in color with distinct lighter green-colored venation and area adjacent to the venation and pubescent petioles.

2 Drawing Sheets

Figure 1:
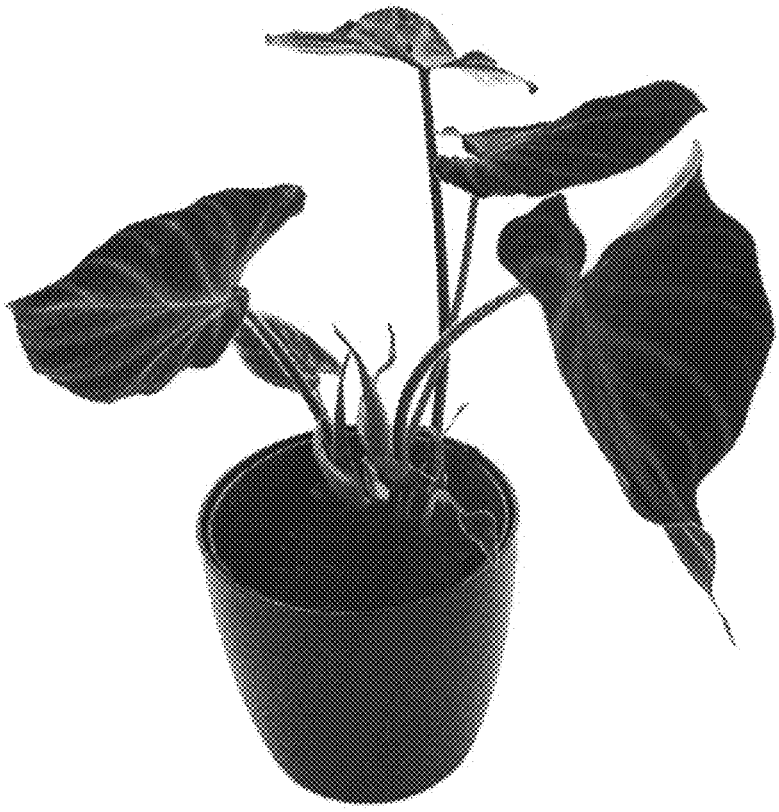

Botanical designation: *Philodendron verrucosum.*
Cultivar denomination: 'PPIPVE007'.

CROSS-REFERENCED TO A RELATED APPLICATION AND STATEMENT REGARDING PRIOR DISCLOSURES BY INVENTOR/APPLICANT AND ASSIGNEE

This application does not claim priority to a European Community Plant Breeders' Rights application filed on Aug. 1, 2019, application number 2019/1885. There have been no offers for sale anywhere in the world prior to the effective filing date of this Application and no accessibility to one of ordinary skill in the art could have been derived from the printed Plant Breeder's Rights documents.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor. Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Philodendron* plant, botanically known as *Philodendron verrucosum* and hereinafter referred to by the name 'PPIPVE007'.

The new *Philodendron* plant is a naturally-occurring whole plant mutation of an unnamed selection of *Philodendron verrucosum*, not patented. The new *Philodendron* plant was discovered and selected by the Inventor in October, 2015 as a single plant from within a population of plants of the unnamed selection in a controlled greenhouse environment in Naaldwijk, The Netherlands.

Asexual reproduction of the new *Philodendron* plant by cuttings in a controlled environment in Naaldwijk, The Netherlands since April, 2016 has shown that the unique features of this new *Philodendron* plant are stable and reproduced true to type in successive generations of asexual reproduction.

SUMMARY OF THE INVENTION

Plants of the new *Philodendron* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'PPIPVE007'. These characteristics in combination distinguish 'PPIPVE007' as a new and distinct *Philodendron* plant:

1. Relatively compact, upright and uniform plant habit.
2. Moderately vigorous growth habit.
3. Relatively large leaves that are dark green in color with distinct lighter green-colored venation and area adjacent to the venation and pubescent petioles.

Plants of the new *Philodendron* differ from plants of the mutation parent selection primarily in growth habit as plants of the new *Philodendron* are more compact and more uniform in habit than plants of the mutation parent selection.

Plants of the new *Philodendron* can be compared to plants of *Philodendron scandens* 'Micans', not patented. Plants of the new *Philodendron* differ from plants of 'Micans' in the following characteristics:

1. Plants of the new *Philodendron* have larger leaves than plants of 'Micans'.
2. Leaf petioles of plants of the new *Philodendron* are pubescent whereas leaf petioles of plants of 'Micans' are glabrous.

BRIEF DESCRIPTION OF THE PHOTOGRAPHS

The accompanying photographs illustrate the overall appearance of the new *Philodendron* plant showing the colors as true as it is reasonably possible to obtain in colored reproductions of this type. Colors in the photographs may differ slightly from the color values cited in the detailed botanical description which accurately describe the colors of the new *Philodendron* plant.

The photograph on the first sheet (FIG. 1 of 2) is a side perspective view of a typical plant of 'PPIPVE007' grown in a container.

Figure 2:
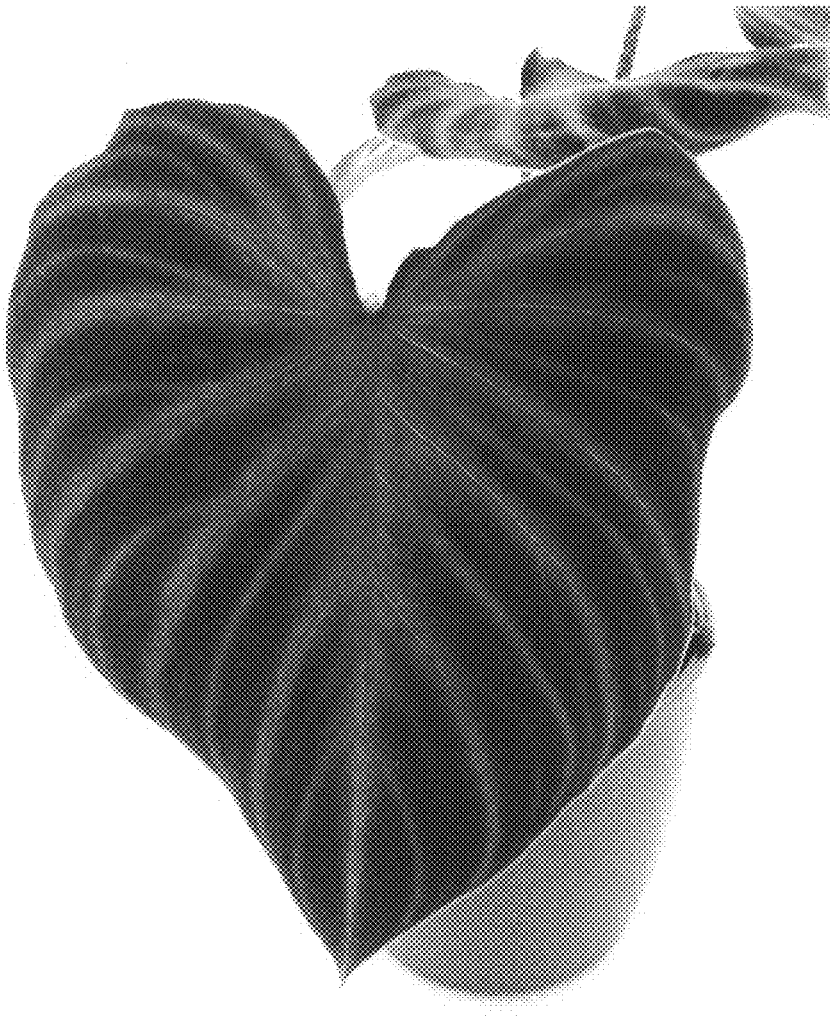

The photograph on the second sheet (FIG. 2 of 2) is a close-up view of a typical plant of 'PPIPVE007'.

DETAILED BOTANICAL DESCRIPTION

The aforementioned photographs and following observations and measurements describe plants grown during the autumn in 13.5-cm containers in a glass-covered greenhouse in Naaldwijk, The Netherlands and under cultural practices typical of commercial *Philodendron* production. During the production of the plants, day temperatures ranged from 10° C. to 25° C. and night temperatures ranged from 4° C. to 15° C. Plants were six months old when the photographs and the detailed description were taken. In the following description, color references are made to The Royal Horticultural Society Colour Chart, 2015 Edition, except where general terms of ordinary dictionary significance are used.

Botanical classification: *Philodendron verrucosum* 'PPIPVE007'.

Parentage: Naturally-occurring whole plant mutation of an unnamed selection of *Philodendron verrucosum*, not patented.

Propagation:

Type: By cuttings.

*Time to initiate roots, summer*.—About 20 days at temperatures about 22° C. to 25° C.

*Time to initiate roots, winter*.—About 25 days at temperatures about 20° C. to 22° C.

*Time to produce a rooted young plant, summer*.—About 45 days at temperatures about 22° C. to 25° C.

*Time to produce a rooted young plant, winter*.—About 60 days at temperatures about 20° C. to 22° C.

*Root description*.—Fibrous, medium in thickness; typically white in color, actual color of the roots is dependent on substrate composition, water quality, fertilizers, substrate temperature and age of roots.

*Rooting habit*.—Moderately freely branching; medium density.

Plant description:

*Plant and growth habit*.—Relatively compact, upright and uniform plant habit; moderately vigorous growth habit; moderate growth rate.

*Plant height*.—About 25.5 cm.

*Plant diameter or spread*.—About 31.9 cm.

*Stem description*.—Branching habit: Plants of the new *Philodendron* are basal branching with about two basal shoots developing per plant. Length: About 6 cm. Diameter: About 7 mm. Internode length: About 3 cm. Aspect: Upright to about 45° from vertical. Strength: Strong. Texture and luster: Smooth, glabrous; glossy. Color, developing: Close to 144C. Color, developed: Close to 143A; color becoming closer to NN137A with subsequent development.

Leaf description:

*Arrangement*.—Alternate; simple.

*Length*.—About 17.5 cm.

*Width*.—About 13.1 cm.

*Shape*.—Cordate.

*Apex*.—Apiculate to abruptly acute.

*Base*.—Deeply cordate to hastate; lobes free.

*Margin*.—Entire; moderately undulate.

*Texture and luster, upper surface*.—Smooth, glabrous; velvety; slightly glossy.

*Texture and luster, lower surface*.—Smooth, glabrous; slightly velvety; slightly glossy.

*Venation pattern*.—Pinnate.

*Color*.—Developing leaves, upper surface: Darker than between 139A and N189A, fading towards the veins to close to 143A; venation, close to 148C to 148D. Developing leaves, lower surface: Close to between 165A and 177A, fading towards the veins to close to 177D; venation, close to 199A to 199B; area adjacent to venation, close to 145B. Fully expanded leaves, upper surface: Darker than 139A; venation, close to 137C; area adjacent to venation, close to 137A. Fully expanded leaves, lower surface: Close to between 177B and 200D; venation, close to between 195A and 199B; area adjacent to venation, close to 145B.

*Petioles*.—Length: About 16.6 cm. Diameter: Proximally, about 5 mm to 7 mm and distally, close to 4 mm. Aspect: Erect to outwardly leaning. Strength: Moderately strong; flexible. Texture and luster, upper and lower surface: Densely pubescent and glandular; matte. Color, upper surface: Close to N199B and fading distally to close to N199A and proximally, close to 147A to darker than 147A. Color, lower surface: Close to 200D and fading proximally to close to N199A.

*Leaf bracts*.—Arrangement: One at the base of each petiole. Length: About 9.3 cm. Width: About 2.7 cm. Shape: Narrowly deltoid with acute apex. Texture and luster: Smooth, glabrous; slightly glossy. Color, upper surface: Close to 182D fading towards the apex to close to between 156A and N187D. Color, lower surface: Close to 180C and 181C fading towards the apex to close to 197B to 197C.

Inflorescence description: To date, inflorescence initiation and development has not been observed on plants of the new *Philodendron*.

Pathogen & pest resistance: To date, plants of the new *Philodendron* not been observed to be resistant to pathogens and pests common to *Philodendron* plants.

Temperature tolerance: Plants of the new *Philodendron* have been observed to tolerate temperatures ranging from about 5° C. to about 40° C. and to be suitable for USDA Hardiness Zones 11 to 13.

It is claimed:

1. A new and distinct *Philodendron* plant named 'PPIPVE007' as illustrated and described.

* * * * *